United States Patent
Hodson

(10) Patent No.: US 11,207,477 B2
(45) Date of Patent: Dec. 28, 2021

(54) FORMULATION AND AEROSOL CANISTERS, INHALERS, AND THE LIKE CONTAINING THE FORMULATION

(71) Applicant: KINDEVA DRUG DELIVERY L.P., St. Paul, MN (US)

(72) Inventor: Peter D. Hodson, Derbyshire (GB)

(73) Assignee: Kindeva Drug Delivery L.P., St. Paul, MN (US)

(*) Notice: Subject to any disclaimer, the term of this patent is extended or adjusted under 35 U.S.C. 154(b) by 15 days.

(21) Appl. No.: 16/613,578

(22) PCT Filed: May 15, 2018

(86) PCT No.: PCT/US2018/032665
§ 371 (c)(1),
(2) Date: Nov. 14, 2019

(87) PCT Pub. No.: WO2018/213244
PCT Pub. Date: Nov. 22, 2018

(65) Prior Publication Data
US 2020/0069895 A1  Mar. 5, 2020

Related U.S. Application Data

(60) Provisional application No. 62/507,313, filed on May 17, 2017.

(51) Int. Cl.
| | |
|---|---|
| *A61M 15/00* | (2006.01) |
| *A61K 9/12* | (2006.01) |
| *A61K 31/137* | (2006.01) |
| *A61K 31/46* | (2006.01) |
| *A61K 47/06* | (2006.01) |
| *A61K 47/34* | (2017.01) |

(52) U.S. Cl.
CPC .......... *A61M 15/009* (2013.01); *A61K 9/124* (2013.01); *A61K 31/137* (2013.01); *A61K 31/46* (2013.01); *A61K 47/06* (2013.01); *A61K 47/34* (2013.01)

(58) Field of Classification Search
CPC .................................................. A61M 15/009
See application file for complete search history.

(56) References Cited

U.S. PATENT DOCUMENTS

| | | |
|---|---|---|
| 8,414,956 B2 | 4/2013 | Jinks |
| 8,479,732 B2 | 7/2013 | Stuart |
| 8,740,014 B2 | 6/2014 | Purkins |
| 8,814,035 B2 | 8/2014 | Stuart |
| 8,815,325 B2 | 8/2014 | David |
| 2003/0180228 A1* | 9/2003 | Cripps .................. A61L 9/04 424/46 |
| 2012/0097159 A1 | 4/2012 | Iyer |
| 2012/0180785 A1* | 7/2012 | Trill .................. A61M 11/04 128/200.23 |
| 2012/0234317 A1 | 9/2012 | Stuart |
| 2014/0299128 A1 | 10/2014 | Jinks |

FOREIGN PATENT DOCUMENTS

| | | |
|---|---|---|
| WO | WO 2001-089616 | 11/2001 |
| WO | WO 2016-164508 | 10/2016 |

OTHER PUBLICATIONS

Atrovent HFA (Highlights of Prescribing Information, Boehringer Ingelheim International GmbH, revised date Feb. 2020). (Year: 2020).*
Atrovent HFA (Safety Data Sheet, Boehringer Ingelheim, revision date of Jun. 3, 2015) (Year: 2015).*
International Search Report for PCT International Application No. PCT/US2018/032665, dated Aug. 7, 2018, 5 pages.

* cited by examiner

*Primary Examiner* — Mark V Stevens
*Assistant Examiner* — Alparslan Asan
(74) *Attorney, Agent, or Firm* — Mueting Raasch Group

(57) ABSTRACT

Formulations containing pharmaceutical active agent, propellant, and water at least partially adsorbed on or absorbed within one or more nylon pellets or nylon components of, for example, an inhaler such as a metered dose inhaler. Canisters, typically sealed canisters, containing such formulations. Inhalers, such as metered dose inhalers, containing such canisters. Methods of making and using the same.

8 Claims, No Drawings

FORMULATION AND AEROSOL CANISTERS, INHALERS, AND THE LIKE CONTAINING THE FORMULATION

CROSS REFERENCE TO RELATED APPLICATIONS

This application is a national stage filing under 35 U.S.C. 371 of PCT/US2018/032,665, filed May 15, 2018, which claims the benefit of U.S. Provisional Patent Application No. 62/507,313, filed May 17, 2017, the disclosures of which are incorporated by reference in their entirety herein.

TECHNICAL FIELD

The present disclosure relates to formulations used for, as an example, an inhaled dosage form, as well as to aerosol canisters, inhalers, metered dose inhalers, and the like containing the same.

BACKGROUND

Inhaler formulations comprising pharmaceutical active agents are known in the art. Known compositions may not be acceptable for use with all drugs. For example, some drugs may not be stable in known compositions.

SUMMARY

A composition can comprise a liquid comprising a propellant, the propellant comprising one or more of HFA-134a and HFA-227, one or more pharmaceutical active agents dissolved or dispersed in the liquid; and one or more nylon pellets, and water. At least some of the water is adsorbed on or absorbed within the one or more nylon pellets.

A method of maintaining a water level in a pressurized aerosol canister can comprise soaking one or more nylon pellets in water to form one or more water soaked pellets, optionally removing water from the surface of the one or more water soaked pellets, forming an aerosol composition by adding the one or more pellets to a composition comprising a pharmaceutical active agent and a liquid comprising one or more of HFA-134a and HFA-227. The aerosol composition can be added to a canister the canister pressurized to form a pressurized canister.

DETAILED DESCRIPTION

Throughout this disclosure, singular forms such as "a," "an," and "the" are often used for convenience; however, it should be understood that the singular forms are meant to include the plural unless the singular alone is explicitly specified or is clearly indicated by the context.

Some terms used in this application have special meanings, as defined herein. All other terms will be known to the skilled artisan, and are to be afforded the meaning that a person of skill in the art at the time of the invention would have given them.

Elements in this specification that are referred to as "common," "commonly used," and the like, should be understood to be common within the context of the compositions, articles, such as inhalers and metered dose inhalers, and methods of this disclosure; this terminology is not used to mean that these features are present, much less common, in the prior art. Unless otherwise specified, only the Background section of this Application refers to the prior art.

The "particle size" of a single particle is the size of the smallest hypothetical hollow sphere that could encapsulate the particle.

The "mass median diameter" of a plurality of particles refers to the value for a particle diameter at which 50% of the mass of particles in the plurality of particles have a particle size smaller than the value and 50% of the mass of particles in the plurality of particle have a particle size greater than the value.

The "ex-actuator size" of a plurality of particles refers to the mass median aerodynamic diameter (sometimes abbreviated as "MMAD") of the plurality of particles after the plurality of particles has passed through the actuator of an inhaler, such as a metered dose inhaler, as measured by the procedure described in the United States Pharmacopeia <601>.

"Weight percent" or "percent by weight," when describing the amount of component in a composition refers to percent weight of the component based on the weight of the entire composition. Weight percent is sometimes abbreviated "wt. %."

"Fine particle dose" is determined according to 2015 United States Pharmacopia test <601>.

"Fine Particle Mass," often abbreviated "FPM," is in this disclosure determined mathematically using Copley Inhaler Testing Data Analysis Software (CITDAS) (Copley Scientific LTD., Nottingham, United Kingdom).

"Fine Particle Fraction," often abbreviated "FPF," is determined according to 2015 United States Pharmacopia test <601> and is calculated as [FPM/(sum of sample content for throat assembly, cups 1-7, MOC, and the filter)]× 100.

The "canister size" of a plurality of particles is used here to refer to the mass mean diameter of the plurality of particles in a canister at the time that the formulation is prepared. Canister size can be determined, for example, using light scattering methods.

The term "nylon pellets" refers to a mass of nylon; this term is used for convenience, but is not intended to convey any particular size or shape of nylon. Nylon pellets can be of any size or shape of nylon.

When the concentration of ipratropium is discussed in this disclosure, for convenience it is referred to in terms of the concentration of ipratropium bromide monohydrate, unless the disclosure specifically refers to another form, such as another salt, hydrate, or anhydrous form. It should therefore be understood that if another form or salt of ipratropium is used, the concentration of that other form or salt should be calculated on a basis relative to ipratropium bromide monohydrate. A person of ordinary skill in the relevant arts can easily perform this calculation by comparing the molecular weight of the form or salt of ipratropium that is used to the molecular weight of ipratropium bromide monohydrate.

Aerosol formulations containing pharmaceutical active agents must be formulated properly in order to provide stability to the pharmaceutical active agent or agents and prevent overly rapid degradation of the pharmaceutical active agent or agents. This is important because overly rapid degradation of the pharmaceutical active agent or agents leads to unacceptable shelf-life of inhalers containing the aerosol formulations.

The stability of pharmaceutical active agents can, in many cases, be enhanced by minimizing the amount of water in the aerosol formulation, for example, by excluding water from the manufacturing process and then sealing the inhaler in a water-resistant pouch, such as a foil pouch, often with a desiccant inside the pouch, to prevent uptake of water from the environment.

This application relates to a newly-recognized problem with that approach. Specifically, some pharmaceutically active agents are not suitably stable when the water level is too low. For example, some pharmaceutical active agents are in the form of hydrates. When the water level is too low, the hydrate can partially or totally dehydrate. The partially or totally dehydrated pharmaceutical active agent can either be pharmaceutically unacceptable or can further degrade.

Thus, this application recognizes a formerly unknown problem, specifically, that the level of water in many aerosol compositions of pharmaceutical active agents must be maintained within particular limits, including a lower limit, in order to maintain stability of some pharmaceutical active agents. This is in contrast to what was formerly understood, namely, that the water content should be kept as low as possible. In response to this problem, the present Application provides aerosol formulations designed to contain water, for example, a pre-determined amount of water, and maintain the water in desirable concentrations. Pressurized canisters containing such solutions, inhalers containing such pressurized canisters, and methods of making such formulations, canisters, and inhalers, are also provided. The aerosol formulations contain a liquid comprising one or more of HFA **134*a* and HFA-227**, a pharmaceutically active agent dissolved or dispersed in the liquid, one or more nylon pellets, and water. At least some of the water is adsorbed on or absorbed in the one or more nylon pellets. The water content can be controlled based on the treatment of the nylon pellets, as described in detail herein.

The nylon pellets can be made from any type of nylon. Nylon nomenclature is well known to those of skill in the art. Nylons are often named with the word "nylon" followed by two numbers, which may be separated by a comma, or by the letters "PA" followed by one or two numbers, wherein two numbers are often separated by a slash. Letters can also be used in the naming scheme, and this nomenclature will be familiar to the artisan or ordinary skill. Typical nylons that may be used include one of nylon 6,6, PA6, PA11, PA12, PA6/66, PA6/6T, PA4T, PA66, PA410, PA6I/6T, PA66/6T, PA12/MACMI, or mixtures thereof. Most commonly, the nylon comprises nylon 6,6. In many cases, the nylon is nylon 6,6.

When the composition is to be filled into a canister, then the nylon pellet is selected so as to fit inside the canister and not be excluded by the opening through which the canister is filled. The nylon pellets can therefore be cylinders, round, pill-shaped, capsule-shaped, flat, or any other convenient shape. In some cases, the nylon pellets are cylinders. Because nylon 6,6 can be obtained as a 5 mm diameter rod, it can be convenient to cut nylon pellets from such a rod, in which case the nylon pellets can have a diameter of 5 mm and any convenient height. Convenient heights can be, for example, from 1 mm to 20 mm.

HFA **134*a* and HFA-227 are common propellants used in aerosol formulations. When they are used as a mixture, any suitable mixture of the two can be used. For example, the amount of HFA-134*a*, on a weight percent basis based on the combined weight of HFA-134*a* and HFA-227, can be at least 10%, at least 20%, at least 30%, at least 40%, at least 50%, at least 60%, at least 70%, or at least 80%. In some cases, the propellant will be primarily HFA-134*a*. In such cases, the HFA-134*a* content of the propellant on a weight percent basis, based on the combined weight of HFA-134*a* and HFA-227, can be at least 90%, such as at least 91%, at least 92%, at least 93%, at least 94%, at least 95%, at least 96%, at least 97% at least 98%, at least 99%, at least 99.25%, at least 99.5%, or at least 99.75%. In some cases, the propellant is HFA-134*a*. The amount of HFA-227, on a weight percent basis based on the combined weight of HFA-134*a* and HFA-227, can be at least 10%, at least 20%, at least 30%, at least 40%, at least 50%, at least 60%, at least 70%, or at least 80%. In some cases, the propellant will be primarily HFA-227. In such cases, the HFA-227 content of the propellant on a weight percent basis, based on the combined weight of HFA-134*a* and HFA-227, can be at least 90%, such as at least 91%, at least 92%, at least 93%, at least 94%, at least 95%, at least 96%, at least 97% at least 98%, at least 99%, at least 99.25%, at least 99.5%, or at least 99.75%. In some cases the propellant is HFA-227**.

The formulation can be a solution. Solution formulations, especially for use in aerosols, can have several advantages over suspension formulations. Such advantages include being homogenous so that users do not need to agitate the formulation to ensure a correct dose. Also, because they are homogeneous, solution formulations provide essentially identical amounts of drug per mass of dose for each dose in an inhaler, whereas inhomogeneous suspensions may lack this consistency.

Solution formulations are not required. Suspension formulations are also possible. In suspension formulations, the pharmaceutical active agent, and in some cases one or more excipients, are wholly or partially dispersed in the liquid rather than being dissolved. Such suspension formulations may, in some cases, have to be agitated or shaken before administrations.

The at least one pharmaceutical active agent can comprise ipratropium. Ipratropium is a cationic material, and is therefore typically used in the form of one or more physiologically acceptable salts or solvates. Ipratropium bromide is the most common salt. The ipratropium bromide is most commonly in the form of a hydrate. Typically, the hydrate is a monohydrate. Thus, ipratropium is usually in the form of ipratropium bromide monohydrate.

The canister size of the particles of ipratropium, such as ipratropium bromide or ipratropium bromide monohydrate, can be any suitable canister size. Exemplary suitable canister sizes can be no less than 1 micrometer, no less than 1.5 micrometers, no less than 2 micrometers, no less than 2.5 micrometers, no less than 3 micrometers, no less than 3.5 micrometers, no less than 4 micrometers, or no less than 4.5 micrometers. Exemplary suitable canister sizes can also be no greater than 5 micrometers, no greater than 4.5 micrometers, no greater than 4.0 micrometers, no greater than 3.5 micrometers, no greater than 3.0 micrometers, no greater than 2.5 micrometers, no greater than 2.0 micrometers, or no greater than 1.5 micrometers. 1 micrometer to 5 micrometers is common.

Ipratropium, such as ipratropium bromide monohydrate, can be present in the composition in solution or as a dispersed particulate. When used in particulate form, the ex-actuator size of the ipratropium particles, such as ipratropium bromide or ipratropium bromide monohydrate, can be any suitable ex-actuator size. Exemplary suitable ex-actuator sizes can be no less than 1 micrometer, no less than 1.5 micrometers, no less than 2 micrometers, no less than 2.5 micrometers, no less than 3 micrometers, no less than 3.5 micrometers, no less than 4 micrometers, or no less than 4.5 micrometers. Exemplary suitable ex-actuator sizes can also be no greater than 5 micrometers, no greater than 4.5 micrometers, no greater than 4.0 micrometers, no greater than 3.5 micrometers, no greater than 3.0 micrometers, no greater than 2.5 micrometers, no greater than 2.0 micrometers, or no greater than 1.5 micrometers. 1 micrometer to 5 micrometers is common.

The ipratropium can be used in any suitable concentration. On a mg/mL basis, typical concentrations are no less than 0.15, no less than 0.2, no less than 0.3, no less than 0.4, no less than 0.5, no less than 0.6, no less than 0.7, no less than 0.8, no less than 0.9, no less than 1.0, no less than 1.1, no less than 1.2, no less than 1.3, no less than 1.4, no less than 1.5, no less than 1.6, no less than 1.7, no less than 1.8, no less than 1.9, or no less than 2.0. Typical concentrations are also no greater than 2.0, no greater than 1.9, no greater than 1.8, no greater than 1.7, no greater than 1.6, no greater than 1.5, no greater than 1.4, no greater than 1.3, no greater than 1.2, no greater than 1.1, no greater than 1.0, no greater than 0.9, no greater than 0.8, no greater than 0.7, no greater than 0.6, or no greater than 0.5. Common concentrations are from 0.2 mg/mL to 1.72 mg/mL. For some applications, a concentration of 0.68 to 0.86 mg/mL is used. For other applications, a concentration of 0.33 to 0.42 mg/mL is used.

Any suitable concentration of ipratropium can be used. When the concentration of ipratropium is expressed in terms of mg/mL of ipratropium bromide monohydrate, then the concentration of ipratropium can be no more than 0.15 mg/ml, no more than 0.14 mg/ml, no more than 0.13 mg/ml, no more than 0.12 mg/ml, no more than 0.11 mg/ml, no more than 0.10 mg/ml, no more than 0.09 mg/ml, no more than 0.08 mg/ml, no more than 0.07 mg/ml, no more than 0.06 mg/ml, or no more than 0.05 mg/ml. The concentration of ipratropium, again expressed in terms of ipratropium bromide monohydrate, can be no less than 0.05 mg/ml, no less than 0.06 mg/ml, no less than 0.07 mg/ml, no less than 0.08 mg/ml, no less than 0.09 mg/ml, no less than 0.1 mg/ml, no less than 0.11 mg/ml, no less than 0.12 mg/ml, or no less than 0.13 mg/ml. Particular embodiments use ipratropium in an amount of about 0.08 mg/ml to about 0.12 mg/ml, such as 0.08 mg/ml to 0.12 mg/ml, about 0.09 mg/ml to about 0.11 mg/ml, such as 0.09 mg/ml to 0.11 mg/ml, about 0.1 mg/ml, or in some cases 0.1 mg/ml. When expressed in terms of wt %, the concentration of ipratropium (in terms of ipratropium bromide monohydrate) is often no greater than 0.015, no greater than 0.014, no greater than 0.0125, or no greater than 0.012. When expressed in terms of wt %, the concentration of ipratropium (in terms of ipratropium bromide monohydrate) is often no less than 0.005, no less than 0.006, no less than 0.0075, no less than 0.008, or no less than 0.01.

The ipratropium can be present in any suitable concentration in the formulation. The concentration is often expressed in terms of ipratropium bromide monohydrate; if a different ipratropium salt or hydrate is used, a person of ordinary skill in the art is able to calculate the concentration of the particular ipratropium salt used in terms of ipratropium bromide monohydrate using the ratio of the molar mass of the ipratropium salt being used to the molar mass of ipratropium bromide monohydrate.

Albuterol, sometimes known as salbutamol, can also be used as the pharmaceutical active agent. The albuterol can be a free base, but is more typically in the form of one or more physiologically acceptable salts or solvates. Albuterol sulfate is most common.

The albuterol, such as albuterol sulfate, is most commonly in particulate form. The canister size of the particles of albuterol, such as albuterol sulfate, can be any suitable canister size. Exemplary suitable canister sizes can be no less than 1 micrometer, no less than 1.0 micrometers, no less than 1.5 micrometers, no less than 2 micrometers, no less than 2.5 micrometers, no less than 3 micrometers, no less than 3.5 micrometers, no less than 4 micrometers, or no less than 4.5 micrometers. Exemplary suitable canister sizes can also be no greater than 5 micrometers, no greater than 4.5 micrometers, no greater than 4.0 micrometers, no greater than 3.5 micrometers, no greater than 3.0 micrometers, no greater than 2.5 micrometers, no greater than 2.0 micrometers, or no greater than 1.5 micrometers. 1 micrometer to 5 micrometers is common.

The ex-actuator size of the albuterol particles, such as albuterol sulfate particles, can be any suitable ex-actuator size. Exemplary suitable ex-actuator sizes can be no less than 1 micrometer, no less than 1.5 micrometers, no less than 2 micrometers, no less than 2.5 micrometers, no less than 3 micrometers, no less than 3.5 micrometers, no less than 4 micrometers, or no less than 4.5 micrometers. Exemplary suitable ex-actuator sizes can also be no greater than 5 micrometers, no greater than 4.5 micrometers, no greater than 4.0 micrometers, no greater than 3.5 micrometers, no greater than 3.0 micrometers, no greater than 2.5 micrometers, no greater than 2.0 micrometers, or no greater than 1.5 micrometers. 1 micrometer to 5 micrometers is common.

The albuterol, such as albuterol sulfate, can be present in any suitable concentration in the formulation. When the concentration of albuterol is expressed in terms of mg/mL, then the concentration of albuterol, based on albuterol sulfate, can be no less than 1.0, no less than 1.5, no less than 1.6, no less than 1.7, no less than 1.8, no less than 1.9, no less than 2.0, no less than 2.1, no less than 2.2, no less than 2.3, no less than 2.4, no less than 2.5, no less than 2.6, no less than 2.7, no less than 2.8, no less than 2.9, no less than 3.0, no less than 3.1, no less than 3.2, no less than 3.3, no less than 3.4, no less than 3.5, no less than 3.6, no less than 3.7, no less than 3.8, no less than 3.9, no less than 4.0, no less than 4.1, no less than 4.2, no less than 4.3, no less than 4.4, no less than 4.5, no less than 4.6, no less than 4.8, no less than 4.9, no less than 5.0, no less than 5.1, no less than 5.1, no less than 5.2, no less than 5.3, no less than 5.4, no less than 5.5, no less than 5.6, no less than 5.7, no less than 5.8, no less than 5.9, no less than 6.0, no less than 6.1, no less than 6.2, no less than 6.3, no less than 6.4, no less than 6.5, no less than 6.6, no less than 6.7, no less than 6.8, no less than 6.9, no less than 7.0, no less than 7.1, no less than 7.2, no less than 7.3, no less than 7.4, no less than 7.5, no less than 7.6, no less than 7.7, no less than 7.8, no less than 7.9, no less than 8.0, no less than 8.1, no less than 8.2, no less than 8.3, no less than 8.4, no less than 8.5, no less than 8.6, no less than 8.7, no less than 8.8, no less than 8.9, no less than 9.0, no less than 9.1, no less than 9.2, no less than 9.3, no less than 9.4, no less than 9.5, no less than 9.6, no less than 9.7, no less than 9.8, no less than 9.9, no less than 10.0, no less than 10.1, no less than 10.2, no less than 10.3, no less than 10.4, no less than 10.5, no less than 10.6, no less than 10.7, no less than 10.8, no less than 10.9, or no less than 11. Also on a mg/mL basis, the concentration of albuterol can be no greater than 11, no greater than 10.9, no greater than 10.8, no greater than 10.7, no greater than 10.6, no greater than 10.5, no greater than 10.4, no greater than 10.3, no greater than 10.2, no greater than 10.1, no greater than 10.0, no greater than 9.9, no greater than 9.8, no greater than 9.7, no greater than 9.6, no greater than 9.5, no greater than 9.4, no greater than 9.3, no greater than 9.2, no greater than 9.1, no greater than 9.0, no greater than 8.9, no greater than 8.8, no greater than 8.7, no greater than 8.6, no greater than 8.5, no greater than 8.4, no greater than 8.3, no greater than 8.2, no greater than 8.1, no greater than 8.0, no greater than 7.9, no greater than 7.8, no greater than 7.7, no greater than 7.6, no greater than 7.5, no greater than 7.4, no greater than 7.3, no greater than 7.2, no greater than 7.1, no greater than 7.0, no greater than 6.9, no greater than 6.8, no greater than 6.7, no greater than 6.6, no greater than 6.5, no greater than 6.4, no greater than 6.3, no greater than 6.2, no greater than 6.1, no greater than 6.0, no greater than 5.9, no greater than 5.8, no greater than 5.7, no greater than 5.6, no greater than 5.5, no greater than 5.4, no greater than 5.3, no greater than 5.2, no greater than 5.1, no greater than 5.0, no greater than 4.9, no greater than 4.8, no greater than 4.7, no greater than 4.6, no greater than 4.5, no greater than 4.4, no greater than 4.3, no greater than 4.2, or no greater than 4.1. Common concentrations are from 1.2 mg/mL to 9.8 mg/mL. For some applications, a concentration of 3.9 to 4.9 mg/mL is employed. For other applications, a concentration of 1.9 to 2.4 mg/mL is employed.

Other pharmaceutical active agents can also be used. The albuterol and ipratropium can be used in combination.

One or more surfactants can also be used. Surfactants are particularly useful to facilitate dispersion of pharmaceutical active agent particles or dissolution of pharmaceutical active agent particles in the formulation. However, surfactant-free formulations can be advantageous for some purposes, and surfactant is not required unless otherwise specified.

When surfactant is included, any pharmaceutically acceptable surfactant can be used. Most such surfactants are suitable for use with an inhaler. Typical surfactants include oleic acid, sorbitan monooleate, sorbitan trioleate, soya lecithin, polyethylene glycol, polyvinylpyrrolidone, or combinations thereof. Oleic acid, polyvinylpyrrolidone, or a combination thereof is most common. A combination of polyvinylpyrrolidone and polyethylene glycol is also commonly employed. When polyvinylpyrrolidone is employed, it can have any suitable molecular weight. Examples of suitable weight average molecular weights are from 10 to 100 kilodaltons, typically from 10 to 50, 10 to 40, 10 to 30 or 10 to 20 kilodaltons. When polyethylene glycol is employed, it can be any suitable grade. PEG 1,000 and PEG 300 are most commonly employed.

When used, the surfactant is typically present, on a weight percent basis, in an amount no less than 0.0001, no less than 0.01, no less than 0.02, no less than 0.03, no less than 0.04, no less than 0.05, no less than 0.06, no less than 0.07, no less than 0.08, no less than 0.09, no less than 0.10, no less than 0.11, no less than 0.12, no less than 0.13, no less than 0.14, no less than 0.15, no less than 0.16, no less than 0.17, no less than 0.18, no less than 0.19, no less than 0.2, no less than 0.21, no less than 0.22, no less than 0.23, no less than 0.24, no less than 0.25, no less than 0.26, no less than 0.27, no less than 0.28, no less than 0.29, no less than 0.3, no less than 0.4, no less than 0.5, no less than 0.6, no less than 0.7, no less than 0.8, no less than 0.9, or no less than 1. The surfactant is also typically present, on a weight percent basis, in an amount no greater than 1, no greater than 0.9, no greater than 0.8, no greater than 0.7, no greater than 0.6, no greater than 0.5, no greater than 0.4, no greater than 0.3, no greater than 0.29, no greater than 0.28, no greater than 0.27, no greater than 0.26, no greater than 0.25, no greater than 0.24, no greater than 0.23, no greater than 0.22, no greater than 0.21, no greater than 0.20, no greater than 0.19, no greater than 0.18, no greater than 0.17, no greater than 0.16, no greater than 0.15, no greater than 0.14, no greater than 0.13, no greater than 0.12, no greater than 0.11, no greater than 0.10, no greater than 0.09, no greater than 0.08, no greater than 0.07, no greater than 0.06, no greater than 0.05, no greater than 0.04, no greater than 0.03, no greater than 0.02, or no greater than 0.01. Concentration ranges can be from 0.0001 wt. % to 1 wt. %, such as 0.001 wt. % to 0.1 wt. %. Particular applications use 0.01 wt. % surfactant.

Particularly, oleic acid can be used in any of the abovementioned concentrations. Particularly, polyvinylpyrrolidone can be used in any of the abovementioned concentrations. Particularly, a combination of polyethylene glycol and polyvinylpyrrolidone can be used in any of the abovementioned concentrations. Particularly, sorbitan trioleate can be used in any of the abovementioned concentrations.

Ethanol can be used to ensure adequate concentration of drug can be dissolved or suspended in the liquid. On a weight percent basis, the amount of ethanol used, if any, is typically up to 20, up to 19, up to 18, up to 17 up to 16, no greater than 15.5, no greater than 15, no greater than 14.5, no greater than 13, no greater than 12, no greater than 11, or no greater than 10. The amount of ethanol used can also be, on a weight percent basis, no less than 10, no less than 11, no less than 12, no less than 13, no less than 14, no less than 14.5, no less than 15, no less than 15.5, no less than 16, no less than 17 or no less than 18. In many cases, the ethanol is about 13 to about 17 percent by weight, 13 to 17 percent by weight, such as about 14 to about 16 percent by weight, 14 to 16 percent by weight, about 14.5 to about 15.5 percent by weight, 14.5 to 15.5 percent by weight, or, in one particular case, about 15 percent by weight or more particularly 15 percent by weight. Ethanol is not always required to obtain a sufficiently high concentration of drug in solution or suspension, and some drugs cannot be formulated with ethanol for stability or other reasons. Ethanol-free formulations can also be employed.

One or more ex-actuator size affecting compounds may be included. Ex-actuator size affecting compounds can change the size of the drug particles as measured after actuation of an inhaler, such as a metered dose inhaler, containing the composition. Surfactants can be used for this purpose. Most pharmaceutically acceptable surfactants are suitable for use with an inhaler. Typical surfactants include oleic acid, sorbitan monooleate, sorbitan trioleate, soya lecithin, polyethylene glycol, polyvinylpyrrolidone, or combinations thereof. Oleic acid, polyvinylpyrrolidone, or a combination thereof is most common. A combination of polyvinylpyrrolidone and polyethylene glycol is also commonly employed. When polyvinylpyrrolidone is employed, it can have any suitable molecular weight. Examples of suitable weight average molecular weights are from 10 to 100 kilodaltons, typically from 10 to 50, 10 to 40, 10 to 30 or 10 to 20 kilodaltons. When polyethylene glycol is employed, it can be any suitable grade. PEG 100 and PEG 300 are most commonly employed. Most commonly, however, the ex-actuator size affecting compound is glycerol.

When used, the ex-actuator size affecting compound, particularly glycerol, can be present in a weight percent basis of no more than 2.0%, no more than 1.9%, no more than 1.8%, no more than 1.7%, no more than 1.6%, no more than 1.55%, no more than 1.5%, no more than 1.45%, no more than 1.4%, no more than 1.3%, no more than 1.2%, no more than 1.1%, no more than 1.0%, no more than 0.9%, no more than 0.8%, or no more than 0.75%. The ex-actuator size affecting compound, particularly glycerol, can be present in a weight percent basis of no less than 1.0%, no less than 1.1%, no less than 1.2%, no less than 1.3%, no less than 1.4%, no less than 1.45%, no less than 1.5%, no less than 1.55%, no less than 1.6%, no less than 1.7%, no less than 1.8%, or no less than 1.9%. Thus, the ex-actuator size affecting compound, particularly glycerol, can be present, on a weight basis, in about 0.7% to about 1.7%, 0.7% to 1.7%, about 0.8% to 1.6%, 0.8% to 1.6%, about 0.9 to about 1.6, 0.9 to 1.6%, about 1.0% to about 1.5%, or 1.0% to 1.5%. Particular examples use either 1.0% or 1.5%.

One or more stabilizing agents can be included. The one or more stabilizing agents can be any agents that increase the stability of the formulation. The stabilizing agents can be, for example, antioxidants such as sacrificial antioxidants. Any pharmaceutically acceptable stabilizing agent can be used. One particular stabilizing agent is citric acid or a salt thereof.

When employed, citric acid or the salt thereof can be present, on a weight percent basis, in amounts of no less than 0.075%, no less than 0.08%, no less than 0.09%, no less than 0.10%, no less than 0.11%, no less than 0.12%, no less than 0.13%, no less than 0.14%, no less than 0.15%, no less than 0.16%, no less than 0.17%, no less than 0.18%, no less than 0.19%, or no less than 0.20%. The citric acid can be present, on a weight percent basis, in amounts of no more than 0.20%, 0.19%, 0.18%, 0.17%, 0.16%, 0.15%, 0.14%, 0.13%, 0.12%, 0.11%, 0.1%, or 0.09%. Exemplary amounts of citric acid, on a weight percent basis, are about 0.12% to about 0.18%, 0.12% to 0.18%, about 0.13% to about 0.17%, 0.13% to 0.17%, about 0.14% to about 0.16%, 0.14% to 0.16%, about 0.15%, or 0.15%. When a salt of citric acid is used, the weight percent values in this paragraph should be understood to be based on the weight of free citric acid (i.e., without considering the weight of the cation). Most commonly, citric acid alone is used.

The compositions can be formed by admixing all of the components. The one or more nylon pellets are typically soaked with water before being added to the composition. Thus, when added to the composition, the nylon pellets have water adsorbed to their surface or absorbed in the pellets, for example, within pores in the pellets or in the spaces between polymer chains such that the water can swell the one or more nylon pellets. In some cases, the surface water can be removed from the one or more nylon pellets, for example by blotting, before addition to the composition.

The amount of water in the pellets can be controlled, for example, by varying the soaking time and the pellet geometry. After soaking and optional surface drying, the amount of water in the pellets can be quantified, for example by gravimetric analysis, before addition to the composition. The total amount of water in the pellets will depend on the desired concentration of water in the composition. The pellets need not be completely saturated with water, and in most cases will not be completely saturated with water.

Once added to the composition, the nylon pellets can release water over time, thereby providing a target concentration of water in the formulation. When the composition is present in a sealed system, particularly an aerosol canister, the use of soaked nylon pellets as described herein can maintain the target level of water in the composition for a prolonged period of time.

Many inhalers are equipped with nylon components, such as valve stems, O-rings, gaskets, or the like. Such components can also be pre-soaked in water and optionally dried of surface water before being affixed to the canister, in which case they can also serve to help maintain the water level in the composition.

In some cases, the pellets can be omitted entirely. In such cases, one or more nylon components of the inhaler, such as the valve stem, an O-ring, a gasket, or the like, are soaked in water to provide the desired water levels. This works the same way as the use of nylon pellets, except that the appropriate amount of water is added by way of adsorption on or absorption into one or more nylon components of the inhaler. All of the remainder of the description herein applies to the use of water-soaked nylon components in the same way as it applies to the use of nylon pellets.

The target concentration range of water in the liquid will depend on the specific pharmaceutical active agent or agents being used. In most cases, the concentration of the water dissolved or dispersed in the liquid is between 50 ppm and 500 ppm based on the liquid and any components dissolved or dispersed in the liquid. This concentration can be achieved by using an appropriate amount of water in the nylon pellets. The appropriate amount of water will depend on the composition of the liquid, including both the propellant choice and the presence or absence of hydrophilic components, such as ethanol and glycerol, and surfactants, such as those discussed above. The actual concentration of water in the liquid can be determined by known means, such as by Karl Fischer analysis. Thus, the person of skill in the art can readily determine how much water should be adsorbed on or absorbed in the pellets by determining the actual water content of the liquid, for example by using Karl Fischer analysis. After determining the actual water content of the liquid, the artisan can increase or decrease the water concentration in the liquid by changing the number, size, or soaking time of the pellets and then re-checking the actual water content of the liquid as an iterative process until the desired water level is reached.

When the pellets are cylindrical in shape, then for pellets of the same diameter the amount of water taken up by the pellets in a given time can increase approximately linearly with the pellet length and be approximately proportional to the pellet surface area. The proportional relationship between water uptake and surface area can hold for other shapes as well. This proportionality may not apply as the pellets approach or reach their saturation limit where they cannot hold any additional water. The skilled artisan using the guidance provided herein will be able to reach the desired water levels within the liquid after routine optimization of the information provided in this disclosure.

The use of soaked nylon as described herein overcomes a practical problem in adding a suitable amount of water to an aerosol composition. As discussed above, the amount of water required is often very low. Depending on the particular pharmaceutical active agent, the tolerance for error can also be very low. For instance, achieving a water content of 250 ppm in a canister that holds a total volume of 10 g means adding only 2.0 mg of water to the canister, which in the art of filling aerosol canisters is considered to be a very small volume that is difficult to add consistently in a repeated manner, such as in a manufacturing setting. This problem is exacerbated when the canister is filled by a cold-filling technique, wherein filling takes place at low temperatures, such as around −60° C., because ambient water readily condenses on or in the canister at such temperatures. In order to prevent such ambient water condensation, the atmosphere at the time of filling is often very dry, for example at a dew point of −80° C. In such dry conditions, it is difficult to accurately add a particular amount water to the canister because some of the water can readily evaporate.

The use of soaked nylon as described herein can ameliorate all of these practical problems by removing the need to add water directly to canisters. Once the desired shape, number, and size of pellets, as well as their soaking time, is determined (such as according to the guidance provided herein), then the pellets can be easily counted out and repeatably added to canisters in a manufacturing setting.

Inhaler

Any of the above-described formulations can be used with any type of inhaler. Metered dose inhalers, sometimes referred to as MDIs, are most common. When the inhaler is a metered dose inhaler, any metered dose inhaler can be employed. Suitable metered dose inhalers are known in the art.

For example, the above-described formulations can be present in a canister, such as a sealed canister. Such sealed canister can contain any of the above-described formulations under pressure, particularly under a pressure greater than ambient atmospheric pressure.

Typical metered dose inhalers for the pharmaceutical formulations described herein contain an aerosol canister fitted with a valve. The canister can have any suitable volume. The canister brimful capacity will depend on the volume of the formulation that is to be used to fill the canister. In typical applications, the canister will have a volume from 5 mL to 500 mL, such as, for example 10 mL to 500 mL, 25 mL to 400 mL, 5 mL to 50 mL, 8 mL to 30 mL, 10 mL to 25 mL, or 50 to 250 mL. The canister will typically have sufficient volume to contain enough medicament for delivering an appropriate number of doses. The appropriate number of doses is discussed herein. The valve is typically affixed, or crimped, onto the canister by way of a cap or ferrule. The cap or ferrule is often made of aluminum or an aluminum alloy, which is typically part of the valve assembly. One or more seals can be located between the canister and the ferrule. The seals can be one or more of O-ring seals, gasket seals, and the like. The valve is typically a metered dose valve. Typical valve sizes range from 20 microliters to 100 microliters. Specific valve size that are commonly employed include 25, 50, 60, and 63 microliter valve sizes.

The container and valve are typically used with an actuator. Most actuators have a patient port, which is typically a mouthpiece, for delivering the formulation contained in the canister. The patient port can be configured in a variety of ways depending on the intended destination of the formulation. For example, a patient port designed for administration to the nasal cavities will generally have an upward slope to direct the formulation to the nose. The actuator is most commonly made out of a plastic material. Typical plastic materials for this purpose include at least one of polyethylene and polypropylene. Typical MDIs have an actuator with a nozzle. In use, the aerosol spray can emerge from this nozzle before exiting the mouthpiece of the actuator. The nozzle can be characterized by an orifice diameter and a jet length. Any suitable orifice diameter can be used. Typical orifice diameters are from 0.2 mm to 0.65 mm, with 0.2 mm to 0.4 mm being particularly useful for delivery of solution formulations, such as the solution formulations discussed herein. Typical orifice jet length is from 0.5 mm to 1 mm. Specific examples include orifice diameters of 0.3 mm, 0.3 mm, or 0.4 mm, any of which can have a jet length of 0.8 mm.

A metered dose valve is typically present, and is often located at least partially within the canister and at least partially in communication with the actuator. Typical metered dose valves include a metering chamber that is at least partially defined by an inner valve body through which a valve stem passes. The valve stem can be biased outwardly by a compression spring to be in a sliding sealing engagement with an inner tank seal and outer diaphragm seal. The valve can also include a second valve body in the form of a bottle emptier. The inner valve body, which is sometimes referred to as the primary valve body, defines, in part, the metering chamber. The second valve body, which is sometimes referred to as the secondary valve body, defines, in part, a pre-metering region (sometimes called a pre-metering chamber) in addition to serving as a bottle emptier. The outer walls of the portion of the metered dose valve that are located within the canister, as well as the inner walls of the canister, defined a formulation chamber for containing the pharmaceutical formulation.

In use, the pharmaceutical formulation can pass from the formulation chamber into the metering chamber. In moving to the metering chamber, the formulation can pass into the above-mentioned pre-metering chamber through an annular space between the secondary valve body (or a flange of the secondary valve body) and the primary valve body. Pressing the valve stem towards the interior of the container actuates the valve, which allows the pharmaceutical formulation to pass from the metering chamber through a side hole in the valve stem, through an outlet in the valve stem, to an actuator nozzle, and finally through the patient port to the patient. When the valve stem is released, more of the pharmaceutical formulation enters the valve, typically into the pre-metering chamber, through an annular space and then into the metering chamber.

The pharmaceutical formulation can be placed into the canister by any known method. The two most common methods are cold filling and pressure filling. In a cold filling process, the pharmaceutical formulation is chilled to an appropriate temperature, which is typically −50° C. to −60° C. for formulations that use propellant HFA 134a, propellant HFA 227, or a combination thereof, and added to the canister. The metered dose valve is subsequently crimped onto the canister. When the canister warms to ambient temperature, the vapor pressure associated with the pharmaceutical formulation increases thereby providing an appropriate pressure within the canister.

In a pressure filling method, the metered dose valve can be first crimped onto the empty canister. Subsequently, the formulation can be added through the valve into the container by way of applied pressure. Alternatively, the non-volatile components can be first added to the empty canister before crimping the valve onto the canister. The propellant can then be added through the valve into the canister by way of applied pressure.

The total dose of ipratropium, such as ipratropium bromide or more particularly ipratropium bromide monohydrate, that is delivered in a single actuation can be any suitable dose depending on the nature of the condition and patient population that the inhaler is designed to treat. Typically, the total dose delivered, in micrograms, is no less than 3, such as no less than 3.25, no less than 3.75, no less than 4, or no less than 4.25. Typically, the total dose delivered, in micrograms, is no more than 6.5, no more than 6.25, no more than 6.0, no more than 5.75, no more than 5.5, no more than 5.25, no more than 5, or no more than 4.75. Most commonly, the dose is from 4 micrograms to 5.5 micrograms per actuation.

Typical inhalers, such as metered dose inhalers, are designed to deliver a specified number of doses of the pharmaceutical formulation. A dose is sometimes deliverable by a single actuation of the inhaler, but can be deliverable by two, three, four, or more actuations. In most cases, the specified number of doses is from 10 to 120, such as from 30-120. One commonly employed metered dose inhaler is designed to provide 60 doses whereby each dose is delivered in two actuations; this can be employed with any of the formulations or inhaler types described herein.

The inhaler, particularly when it is a metered dose inhaler, can contain a dose counter for counting the number of doses. Suitable dose counters are known in the art, and are described in, for example, U.S. Pat. Nos. 8,740,014, 8,479, 732, and U.S. Patent Application Publication No. 2012/0234317, and U.S. Pat. No. 8,814,035, all of which are incorporated by reference for their disclosures of dose counters.

One exemplary dose counter, which is described in detail in U.S. Pat. No. 8,740,014 (which is hereby incorporated by reference for its disclosure of the dose counter) has a fixed ratchet element and a trigger element that is constructed and arranged to undergo reciprocal movement coordinated with the reciprocal movement between an actuation element in an inhaler and the dose counter. The reciprocal movement typically comprises an outward stroke (outward being with respect to the inhaler) and a return stroke. The return stroke returns the trigger element to the position that it was in prior to the outward stroke. A counter element is also included in this type of dose counter. The counter element is constructed and arranged to undergo a predetermined counting movement each time a dose is dispensed. The counter element is biased towards the fixed ratchet and trigger elements and is capable of counting motion in a direction that is substantially orthogonal to the direction of the reciprocal movement of the trigger element.

The counter element in the above-described dose counter comprises a first region for interacting with the trigger member. The first region comprises at least one inclined surface that is engaged by the trigger member during the outward stroke of the trigger member. This engagement during the outward stroke causes the counter element to undergo a counting motion. The counter element also comprises a second region for interacting with the ratchet member. The second region comprises at least one inclined surface that is engaged by the ratchet element during the return stroke of the trigger element causing the counter element to undergo a further counting motion, thereby completing a counting movement. The counter element is normally in the form of a counter ring, and is advanced partially on the outward stroke of the trigger element, and partially on the return stroke of the trigger element. As the outward stroke of the trigger typically corresponds to the depression of a valve stem that causes firing of the valve (and, in the case of a metered dose inhaler, also meters the contents) and the return stroke typically corresponds to the return of the valve stem to its resting position, this dose counter allows for precise counting of doses.

Another suitable dose counter, which is described in detail in U.S. Pat. No. 8,479,732 (which is incorporated by reference for its disclosure of dose counters) is specially adapted for use with a metered dose inhaler. This dose counter includes a first count indicator having a first indicia bearing surface. The first count indicator is rotatable about a first axis. The dose counter also includes a second count indicator having a second indicia bearing surface. The second count indicator is rotatable about a second axis. The first and second axes are disposed such that they form an obtuse angle. The obtuse angle mentioned above can be any obtuse angle, but is advantageously 125 to 145 degrees. The obtuse angle permits the first and second indicia bearing surface to align at a common viewing area to collectively present at least a portion of a medication dosage count. One or both of the first and second indicia bearing surfaces can be marked with digits, such that when viewed together through the viewing area the numbers provide a dose count. For example, one of the first and second indicia bearing surface may have "hundreds" and "tens" place digits, and the other may have "ones" place digits, such that when read together the two indicia bearing surfaces provide a number between 000 and 999 that represents the dose count.

Yet another suitable dose counter is described in U.S. Patent Application Publication No. 2012/0234317 (hereby incorporated by reference for its disclosure of dose counters). Such a dose counter includes a counter element that undergoes a predetermined counting motion each time a dose is dispensed. The counting motion is typically vertical or essentially vertical. A count indicating element is also included. The count indicating element, which undergoes a predetermined count indicating motion each time a dose is dispensed, includes a first region that interacts with the counter element.

The counter element has regions for interacting with the count indicating element. Specifically, the counter element comprises a first region that interacts with a count indicating element. The first region includes at least one surface that it engaged with at least one surface of the first region of the aforementioned count indicating element. The first region of the counter element and the first surface of the count inducing element are disposed such that the count indicating member completes a count indicating motion in coordination with the counting motion of the counter element, during and induced by the movement of the counter element, the count inducing element undergoes a rotational or essentially rotational movement. In practice, the first region of the counter element or the counter indicating element can comprise, for example, one or more channels. A first region of the other element can comprise one or more protrusions adapted to engage with said one or more channels.

Yet another dose counter is described in U.S. Pat. No. 8,814,035 (hereby incorporated by reference for its disclosure of dose counters). Such a dose counter is specially adapted for use with an inhaler with a reciprocal actuator operating along a first axis. The dose counter includes an indicator element that is rotatable about a second axis. The indicator element is adapted to undergo one or more predetermined count-indicating motions when one or more doses are dispensed. The second axis is at an obtuse angle with respect to the first axis. The dose counter also contains a worm rotatable about a worm axis. The worm is adapted to drive the indicator element. It may do this, for example, by containing a region that interacts with and enmeshes with a region of the indicator element. The worm axis and the second axis do not intersect and are not aligned in a perpendicular manner. The worm axis is also, in most cases, not disposed in coaxial alignment with the first axis. However, the first and second axes may intersect.

At least one of the various internal components of an inhaler, such as a metered dose inhaler, as described herein, such as one or more of the canister, valve, gaskets, seals, O-rings, and the like, can be coated with one or more coatings. Some of these coatings provide a low surface energy. Such coatings are not required because they are not necessary for the successful operation of all inhalers.

Some coatings that can be used are described in U.S. Pat. Nos. 8,414,956, 8,815,325 and U.S. Patent Application No. 2012/0097159, all of which are incorporated by reference for their disclosure of coatings for inhalers and inhaler components.

A first acceptable coating can be provided by the following method:
    a) providing one or more component of the inhaler, such as the metered dose inhaler,
    b) providing a primer composition comprising a silane having two or more reactive silane groups separated by an organic linker group,
    c) providing a coating composition comprising an at least partially fluorinated compound, d) applying the primer composition to at least a portion of the surface of the component,
e) applying the coating composition to the portion of the surface of the component after application of the primer composition.

The at least partially fluorinated compound will usually comprise one or more reactive functional groups, with the one or each one reactive functional group usually being a reactive silane group, for example a hydrolysable silane group or a hydroxysilane group. Such reactive silane groups allow reaction of the partially fluorinated compound with one or more of the reactive silane groups of the primer. Often such reaction will be a condensation reaction.

One exemplary silane that can be used has the formula $$X_{3-m}(R^1)_m Si\text{-}Q\text{-}Si(R^2)_k X_{3-k}$$

wherein $R^1$ and $R^2$ are independently selected univalent groups, X is a hydrolysable or hydroxy group, m and k are independently 0, 1, or 2 and Q is a divalent organic linking group.

Useful examples of such silanes include one or a mixture of two or more of 1,2-bis(trialkoxysilyl) ethane, 1,6-bis(trialkoxysilyl) hexane, 1,8-bis(trialkoxysilyl) octane, 1,4-bis(trialkoxysilylethyl)benzene, bis(trialkoxysilyl)itaconate, and 4,4'-bis(trialkoxysilyl)-1,1'-diphenyl, wherein any trialkoxy group may be independently trimethoxy or triethoxy.

The coating solvent usually comprises an alcohol or a hydrofluoroether.

If the coating solvent is an alcohol, preferred alcohols are $C_1$ to $C_4$ alcohols, in particular, an alcohol selected from ethanol, n-propanol, or iso-propanol or a mixture of two or more of these alcohols.

If the coating solvent is a hydrofluoroether, it is preferred if the coating solvent comprises a $C_4$ to $C_{10}$ hydrofluoroether. Generally, the hydrofluoroether will be of formula $$C_g F_{2g+1} O C_h H_{2h+1}$$

wherein g is 2, 3, 4, 5, or 6 and h is 1, 2, 3 or 4. Examples of suitable hydrofluoroethers include those selected from the group consisting of methyl heptafluoropropylether, ethyl heptafluoropropylether, methyl nonafluorobutylether, ethyl nonafluorobutylether and mixtures thereof.

The polyfluoropolyether silane is typically of the formula $$R^f Q^1_v [Q^2_w\text{---}[C(R^4)_2\text{---}Si(X)_{3-x}(R^5)_x]_y]_z$$

wherein:
$R^f$ is a polyfluoropolyether moiety;
$Q^1$ is a trivalent linking group;
each $Q^2$ is an independently selected organic divalent or trivalent linking group;
each $R^4$ is independently hydrogen or a $C_{1-4}$ alkyl group;
each X is independently a hydrolysable or hydroxyl group;
$R^5$ is a $C_{1-8}$ alkyl or phenyl group;
v and w are independently 0 or 1, x is 0 or 1 or 2; y is 1 or 2; and z is 2, 3, or 4.

The polyfluoropolyether moiety $R^f$ can comprise perfluorinated repeating units selected from the group consisting of —$(C_nF_{2n}O)$—, —$(CF(Z)O)$—, —$(CF(Z)C_nF_2O)$—, —$(C_nF_{2n}CF(Z)O)$—, —$(CF_2CF(Z)O)$—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6. In particular, n can be an integer from 1 to 4, more particularly from 1 to 3. For repeating units including Z the number of carbon atoms in sequence may be at most four, more particularly at most 3. Usually, n is 1 or 2 and Z is a —$CF_3$ group, more particularly wherein z is 2, and $R^f$ is selected from the group consisting of —$CF_2O(CF_2O)_m(C_2F_4O)_pCF_2$—, —$CF(CF_3)O(CF(CF_3)CF_2O)_pCF(CF_3)$—, —$CF_2O(C_2F_4O)_p CF_2$—, —$(CF_2)_3O(C_4F_8O)_p(CF_2)_3$—, —$CF(CF_3)$—$(OCF_2CF(CF_3))_pO$—$C_tF_{2t}$—$O(CF(CF_3)CF_2O)_pCF(CF_3)$—, wherein t is 2, 3 or 4 and wherein m is 1 to 50, and p is 3 to 40.

A cross-linking agent can be included. Typical cross-linking agents include tetramethoxysilane; tetraethoxysilane; tetrapropoxysilane; tetrabutoxysilane; methyl triethoxysilane; dimethyldiethoxysilane; octadecyltriethoxysilane; 3-glycidoxy-propyltrimethoxysilane; 3-glycidoxy-propyltriethoxysilane; 3-aminopropyl-trimethoxysilane; 3-aminopropyl-triethoxysilane; bis (3-trimethoxysilylpropyl) amine; 3-aminopropyl tri(methoxyethoxyethoxy) silane; N (2-aminoethyl)3-aminopropyltrimethoxysilane; bis (3-trimethoxysilylpropyl) ethylenediamine; 3-mercaptopropyltrimethoxysilane; 3-mercaptopropyltriethoxysilane; 3-trimethoxysilyl-propylmethacrylate; 3-triethoxysilypropylmethacrylate; bis (trimethoxysilyl) itaconate; allyltriethoxysilane; allyltrimethoxysilane; 3-(N-allylamino)propyltrimethoxysilane; vinyltrimethoxysilane; vinyltriethoxysilane; and mixtures thereof.

The component to be coated can be pre-treated before coating, typically by cleaning. Cleaning can be by way of a solvent, typically a hydrofluoroether, e.g. HFE72DE, or an azeotropic mixture of about 70% w/w trans-dichloroethylene; 30% w/w of a mixture of methyl and ethyl nonafluorobutyl and nonafluoroisobutyl ethers.

The above-described first acceptable coating is particularly useful for coating valve components, including one or more of valve stems, bottle emptiers, springs, and tanks, as well as canisters, such as metered dose inhalers, as described herein. This coating system can be used with any type of inhaler and any formulation described herein.

A second type of coating that can be used comprises a polyphenylsulphone. The polyphenylsulphone typically has the following chemical structure

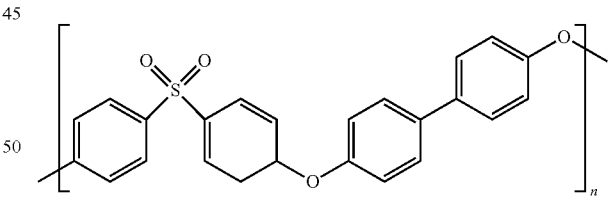

In this structure, n is the number of repeat units, which is typically sufficient to provide a weight average molecular weight from 10,000 to 80,000 daltons, for example, from 10,000 to 30,000 daltons.

Other polymers, such as polyethersulphones, fluoropolymers such as PTFE, FEP, or PFA, can also be included. However, such other polymers are optional, and it is often advantageous to exclude them.

Polyphenylsulphones can be difficult to apply by a solvent casting process. Thus, a special solvent system that is viable for use in a manufacturing setting can be employed for coating polyphenylsulphones. One such solvent system employs a (1) first solvent that has a Hildebrand Solubility Parameter of at least 20.5 $MPa^{0.5}$ and at most 25 $MPa^{0.5}$, such as from 21 MPa$^{0.5}$ to 23.5 MPa$^{0.5}$; and (2) at least 20% by volume, often greater than 70% or greater than 80% by volume, of at least one 5-membered aliphatic, cyclic, or heterocyclic ketone based on the total volume of the solvent system. Optionally, a third component, namely a linear aliphatic ketone, can be included in amounts less than 5% by volume of the total volume of the solvent system.

Any first solvent that has a Hildebrand Solubility Parameter of at least 20.5 MPa$^{0.5}$ and at most 25 MPa$^{0.5}$ can be used, so long as the other components of the solvent system are as stated above. Some such first solvents are also 5-membered aliphatic, cyclic, or heterocyclic ketones, in which case the first solvent and the 5-membered aliphatic, cyclic, or heterocyclic ketone can be the same material. Other such solvents include acetonitrile.

The 5-membered aliphatic, cyclic, or heterocyclic ketone is typically a gamma lactone, such as gamma-butyrolactone, or a gamma lactam, such as a pyrolidone like 2-pyrrolidone, or an alkyl substituted 2-pyrrolidone like N-alkyl-2-pyrrolidones such as N-methyl-2-pyrrolidine (sometimes known by the acronym NMP). Other examples of 5-membered aliphatic, cyclic, or heterocyclic ketone that can be used include 2-methyl cyclopentanone, 2-ethyl cyclopentanone, and 2-[1-(5-methyl-2-furyl)butyl]cyclopentanone. Cyclopentanone is the most commonly used material.

The optional linear aliphatic ketone can be any linear aliphatic ketone, and is typically acetone, although methyl ethyl ketone is also frequently employed.

The above-described second acceptable coating can be used on any type of inhaler, but is particularly useful for components of metered dose inhalers.

A third acceptable coating can be used to lower the surface energy of any component of an inhaler, such as a metered dose inhaler, but is particularly useful for valve stems, particularly those made of acetal polymer, as well as for stainless steel or aluminum components, particularly those used in canisters.

Such a coating can be formed on a component of an inhaler by the following process:
a) forming a non-metal coating on at least a portion of a surface of the medicinal inhalation device or a component of a medicinal inhalation device, respectively, said coating having at least one functional group;
b) applying to at least a portion of a surface of the non-metal coating a composition comprising an at least partially fluorinated compound comprising at least one functional group; and
c) allowing at least one functional group of the at least partially fluorinated compound to react with at least one functional group of the non-metal coating to form a covalent bond.

The at least one functional group of the non-metal coating is typically a hydroxyl group or silanol group. In most cases, the non-metal coating has a plurality of functional groups, particularly silanol groups, and can be formed, for example by plasma coating an organosilicone with silanol groups on the inhaler or one or more inhaler components. Typical organosilicon compounds include trimethylsilane, triethylsilane, trimethoxysilane, triethoxysilane, tetramethylsilane, tetraethylsilane, tetramethoxysilane, tetraethoxysilane, hexamethylcyclotrisiloxane, tetramethylcyclotetrasiloxane, tetraethylcyclotetrasiloxane, octamethylcyclotetrasiloxane, hexamethyldisiloxane, bistrimethylsilylmethane, and mixtures thereof. Most commonly, one or more of trimethylsilane, triethylsilane, tetramethylsilane, tetraethylsilane, bistrimethylsilylmethane are employed, with tetramethylsilane being most common. In addition to the organosilicon, the plasma can contain one or more of oxygen, a silicon hydride, particularly silicon tetrahydride, disilane, or a mixture thereof, or both. After deposition, the non-metal coating can be a diamond-like glass or carbon-like glass containing, on a hydrogen free basis, 20 atomic percent or more of carbon and 30 atomic percent of more of silicon and oxygen combined.

The non-metal coating is often exposed to an oxygen plasma or corona treatment before applying the partially fluorinated compound. Most typically, an oxygen plasma treatment under ion bombardment conditions is employed.

The at least partially fluorinated compound often contains one or more hydrolysable groups, such as oxyalkyl silanes, typically ethyoxy or methoxy silanes. A polyfluoropolyether segment, which in particular cases is a perfluorinated polyfluoroether, is typically used. Poly(perfluoroethylene) glycol is most common. Thus, the at least partially fluorinated compound can include a polyfluropolyether linked to one or more functional silanes by way of, for example, a carbon-silicon, nitrogen-silicon, or sulfur-silicon bond.

Examples of at least partially fluorinated compounds that can be used include those having the following formula:

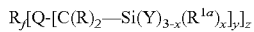

wherein:
$R_f$ is a monovalent or multivalent polyfluoropolyether segment;
Q is an organic divalent or trivalent linking group;
each R is independently hydrogen or a $C_{1-4}$ alkyl group;
each Y is independently a hydrolysable group;
$R^{1a}$ is a $C_{1-8}$ alkyl or phenyl group;
x is 0 or 1 or 2;
y is 1 or 2; and
z is 1, 2, 3, or 4.

Typically, $R_f$ comprises perfluorinated repeating units selected from the group consisting of —$(C_nF_{2n}O)$—, —$(CF(Z)O)$—, —$(CF(Z)C_nF_{2n}O)$—, —$(C_nF_{2n}CF(Z)O)$—, —$(CF_2CF(Z)O)$—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic and have 1 to 5 carbon atoms and up to 4 oxygen atoms when oxygen-containing or oxygen-substituted and wherein for repeating units including Z the number of carbon atoms in sequence is at most 6. Particular examples of this compound are those where z is 1, $R^f$ is selected from the group consisting of $C_3F_7O(CF(CF_3)CF_2O)_pCF(CF_3)$—, $CF_3O(C_2F_4O)_pCF_2$—, $C_3F_7O(CF(CF_3)CF_2O)_pCF_2CF_2$—, $C_3F_7O(CF_2CF_2CF_2O)_pCF_2CF_2$—, $C_3F_7O(CF_2CF_2CF_2O)_pCF(CF_3)$— and $CF_3O(CF_2CF(CF_3)O)_p(CF_2O)X$—, wherein X is $CF_2$—, $C_2F_4$—, $C_3F_6$—, or $C_4F_8$— and wherein the average value of p is 3 to 50. Other particular examples include those wherein z is 2, $R_f$ is selected from the group consisting of —$CF_2O(CF_2O)_m(C_2F_4O)_pCF_2$—, —$CF(CF_3)O(CF(CF_3)CF_2O)_pCF(CF_3)$—, —$CF_2O(C_2F_4O)_pCF_2$—, —$(CF_2)_3O(C_4F_8O)_p(CF_2)_3$—, —$CF(CF_3)$—$(OCF_2CF(CF_3))_pO$—$C_tF_{2t}$—$O(CF(CF_3)CF_2O)_pCF(CF_3)$—, wherein t is 2, 3 or 4 and wherein m is 1 to 50, and p is 3 to 40. Most commonly $R_f$ is one of —$CF_2O(CF_2O)_m(C_2F_4O)_pCF_2$—, —$CF_2O(C_2F_4O)_pCF_2$—, and —$CF(CF_3)$—$(OCF_2CF(CF_3))_pO$—$(C_tF_{2t})$—$O(CF(CF_3)CF_2O)_pCF(CF_3)$—, t is 2, 3, or 4, and the average value of m+p or p+p or p is from about 4 to about 24. Q is commonly selected from the group consisting of —C(O)N(R)—$(CH_2)_k$—, —S(O)$_2$N(R)—$(CH_2)_k$—, —$(CH_2)_k$—, —$CH_2O$—$(CH_2)_k$—, —C(O)S—$(CH_2)_k$—, —$CH_2OC(O)N$(R)—$(CH_2)_k$—, and

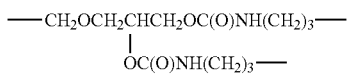

when R is hydrogen or $C_{1-4}$ alkyl, and k is 2 to about 25. In other common cases, Q is selected from the group consisting of —C(O)N(R)(CH$_2$)$_2$—, —OC(O)N(R)(CH$_2$)$_2$—, —CH$_2$O(CH$_2$)$_2$—, or —CH$_2$—OC(O)N(R)—(CH$_2$)$_2$—, R is hydrogen or $C_{1-4}$ alkyl, and y is 1.

Upon applying appropriate at least partially fluorinated compounds to the non-metallic coating, at least one covalent bond can form between the two, thereby completing the coating.

Yet another suitable coating is fluorinated ethylene propylene copolymer, sometimes known as FEP. FEP coatings are particularly useful for coating one or more internal surfaces of a canister, and can be used in association with other coatings that can be applied to either other internal surfaces of a canister or to other components of the inhaler.

Packaging

The inhaler containing the canister and formulation can be stored by sealing within a moisture-barrier pouch. The moisture-barrier pouch can have one or more layers, and typically has at least one moisture barrier layer. The moisture barrier layer can be any layer that inhibits or prevents moisture from moving through the pouch. The moisture barrier layer is typically aluminum foil, but other moisture barrier layers, such as polymeric moisture barrier layers, can also be employed. It is also possible to store the inhaler in other ways, so the moisture barrier pouch is not used in all cases.

Contrary to the teachings of the prior art, the moisture barrier pouch, when used, typically does not include a desiccant within the pouch. This is because, contrary to the suggestions in the prior art that the water level should be minimized, the inventors have recognized that too low of a water level can induce degradation of some drugs. A desiccant that removes water from the formulation can, therefore, actually have a destabilizing effect on the drug in cases where the drug is sensitive to dry conditions. Instead, the nylon pellets as described herein can be used to maintain the water level and prevent overdrying of the formulation.

LIST OF EXEMPLARY EMBODIMENTS

The following embodiments are meant to be illustrative, and are not intended to be limiting unless otherwise specified.

1. A composition comprising
a liquid comprising a propellant, the propellant comprising one or more of HFA-134a and HFA-227
one or more pharmaceutical active agents dissolved or dispersed in the liquid; and
one or more nylon pellets; and
water, wherein
at least some of the water is adsorbed on or absorbed within the one or more nylon pellets.

1a. A composition comprising
a liquid comprising a propellant, the propellant comprising one or more of HFA-134a and HFA-227
one or more pharmaceutical active agents dissolved or dispersed in the liquid;
one or more nylon components; and
water, wherein
at least some of the water is adsorbed on or absorbed within the one or more nylon components.

2. The composition of embodiment 1, wherein at least one of the one or more pharmaceutical active agents is a hydrate.

3. The composition of any of the preceding embodiments, wherein at least one of the one or more pharmaceutical active agents is a hydrate of ipratropium or a hydrate of an ipratropium salt.

4. The composition of any of the preceding embodiments, wherein at least one of the one or more pharmaceutical active agents is ipratropium or a salt or hydrate thereof.

5. The composition of any of the preceding embodiments, wherein at least one of the one or more pharmaceutical active agents is ipratropium bromide.

6. The composition of any of the preceding embodiments, wherein at least one of the one or more pharmaceutical active agents is ipratropium bromide monohydrate.

7. The composition of any of the preceding embodiments, wherein the concentration of ipratropium, expressed in terms of ipratropium bromide monohydrate, is no more than 0.15 mg/ml, no more than 0.14 mg/ml, no more than 0.13 mg/ml, no more than 0.12 mg/ml, no more than 0.11 mg/ml, no more than 0.10 mg/ml, no more than 0.09 mg/ml, no more than 0.08 mg/ml, no more than 0.07 mg/ml, no more than 0.06 mg/ml, or no more than 0.05 mg/ml.

8. The composition of any of the preceding embodiments, wherein the concentration of ipratropium, expressed in terms of ipratropium bromide monohydrate, is no less than 0.05 mg/ml, no less than 0.06 mg/ml, no less than 0.07 mg/ml, no less than 0.08 mg/ml, no less than 0.09, no less than 0.1 mg/ml, no less than 1.1 mg/ml, no less than 1.2 mg/ml, or no less than 1.3 mg/ml.

9. The composition of any of the preceding embodiments, wherein the concentration of ipratropium, expressed in terms of ipratropium bromide monohydrate, is about 0.08 mg/ml to about 0012 mg/ml, 0.08 mg/ml to 0.12 mg/ml, about 0.09 mg/ml to about 0.11 mg/ml, or 0.09 mg/ml to 0.11 mg/ml.

9a. The composition of any of the preceding embodiments, wherein the concentration of ipratropium, expressed in terms of ipratropium bromide monohydrate, is about 0.1 mg/ml or 0.1 mg/ml.

9b. The composition of any preceding embodiment, wherein the concentration of ipratropium expressed as wt % of ipratropium bromide monohydrate is no less than 0.005, no less than 0.006, no less than 0.0075, no less than 0.008, or no less than 0.01.

9c. The composition of any of the preceding embodiments wherein the concentration of ipratropium expressed as wt % of ipratropium bromide monohydrate is no greater than 0.015, no greater than 0.014, no greater than 0.0125, or no greater than 0.012.

10. The composition of any of the preceding embodiments wherein the weight percent of ethanol is no greater than 20, no greater than 19, no greater than 18, no greater than 17, no greater than 16, no greater than 15.5, no greater than 15, no greater than 14.5, no greater than 13, no greater than 12, no greater than 11, or no greater than 10.

11. The composition of any of the preceding embodiments, wherein the weight percent of ethanol is no less than 10, no less than 11, no less than 12, no less than 13, no less than 14, no less than 14.5, no less than 15, no less than 15.5, no less than 16, no less than 17 or no less than 18.

12. The composition of any of the preceding embodiments wherein the weight percent of ethanol is from about 13 to about 17, 13 to 17, about 14 to about 16, 14 to 16, about 14.5 to about 15.5, or 14.5 to 15.5.

13. The composition of any of the preceding embodiments, wherein the weight percent of ethanol is about 15 or more particularly 15.

14. The composition of any of the preceding embodiments, wherein the weight percent of citric acid or salt thereof based on the weight of citric acid, is less than 0.075%, no less than 0.08%, no less than 0.09%, no less than 0.10%, no less than 0.11%, no less than 0.12%, no less than 0.13%, no less than 0.14%, no less than 0.15%, no less than 0.16%, no less than 0.17%, no less than 0.18%, no less than 0.19%, or no less than 0.20%.

15. The composition of any of the preceding embodiments, wherein the weight percent of citric acid, or salt thereof based on the weight of citric acid, is no more than 0.20%, no more than 0.19%, no more than 0.18%, no more than 0.17%, no more than 0.16%, no more than 0.15%, no more than 0.14%, no more than 0.13%, no more than 0.12%, no more than 0.11%, no more than 0.1%, or no more than 0.09%.

16. The composition of any of the preceding embodiments, wherein the weight percent of citric acid, or salt thereof based on the weight of citric acid, is 0.12% to about 0.18%, 0.12% to 0.18%, about 0.13% to about 0.17%, 0.13% to 0.17%, about 0.14% to about 0.16%, 0.14% to 0.16%, about 0.15%, or 0.15%.

17. The composition of any of the preceding embodiments, wherein the weight percent of citric acid or salt thereof, based on the weight of citric acid, is, about 0.15%, or 0.15%.

18. The composition of any of the preceding embodiments, wherein the citric acid or salt thereof is citric acid.

19. The composition of any of the preceding embodiments, wherein glycerol is present, on a weight percent basis, in an amount no more than 2.0%, no more than 1.9%, no more than 1.8%, no more than 1.7%, no more than 1.6%, no more than 1.55%, no more than 1.5%, no more than 1.45%, no more than 1.4%, no more than 1.3%, no more than 1.2%, no more than 1.1%, no more than 1.0%, no more than 0.9%, no more than 0.8%, or no more than 0.75%. Thus, the ex-actuator size affecting compound, particularly glycerol, can be present, on a weight percent basis, in about 0.7% to about 1.7%, 0.7% to 1.7%, about 0.8% to 1.6%, 0.8% to 1.6%, about 0.9 to about 1.6, 0.9 to 1.6, about 1.0% to about 1.5%, or 1.0% to 1.5%.

20. The composition of any of the preceding embodiments, wherein glycerol is present, on a weight percent basis, in an amount no less than 1.0%, no less than 1.1%, no less than 1.2%, no less than 1.3%, no less than 1.4%, no less than 1.45%, no less than 1.5%, no less than 1.55%, no less than 1.6%, no less than 1.7%, no less than 1.8%, or no less than 1.9%.

21. The composition of any of the preceding embodiments wherein the glycerol is present, on a weight percent basis, in about 0.7% to about 1.7%, 0.7% to 1.7%, about 0.8% to 1.6%, 0.8% to 1.6%, about 0.9 to about 1.6, or 0.9% to 1.6%.

22. The composition of any of the preceding embodiments wherein the glycerol present, on a weight percent basis, in about 1.0% to about 1.5%, or 1.0% to 1.5%.

23. The composition of embodiment 22 wherein the glycerol is present, on a weight percent basis, in about 1.0%, more particularly 1%, or wherein the glycerol is present, on a weight percent basis, in about 1.5%, more particularly 1.5%.

24. The composition of any preceding embodiment wherein the composition loses less than 5 wt % of the ipratropium content after six months of storage inside an aerosol canister at a temperature of 25° C. and a relative humidity of 60%.

25. The composition of any of the preceding embodiments, wherein the amount of HFA-134*a* in the propellant is, on a weight percent basis, at least 10%, at least 20%, at least 30%, at least 40%, at least 50%, at least 60%, at least 70%, at least 80%, or at least 90%, such as at least 91%, at least 92%, at least 93%, at least 94%, at least 95%, at least 96%, at least 97%, at least 98%, at least 99%, at least 99.25%, at least 99.5%, or at least 99.75%, based on the total weight of the propellant.

26. The composition of any of the preceding embodiments, wherein the amount of HFA-227 in the propellant is, on a weight percent basis, at least 10%, at least 20%, at least 30%, at least 40%, at least 50%, at least 60%, at least 70%, at least 80%, or at least 90%, such as at least 91%, at least 92%, at least 93%, at least 94%, at least 95%, at least 96%, at least 97%, at least 98%, at least 99%, at least 99.25%, at least 99.5%, or at least 99.75%, based on the total weight of the propellant.

27. The composition of any of the preceding embodiments, wherein the composition further comprises albuterol.

28. The composition of any of the preceding embodiments, wherein the nylon comprises one or more of nylon 6,6, PA6, PA11, PA12, PA6/66, PA6/6T, PA4T, PA66, PA410, PA6I/6T PA66/6T, PA12/MACMI, or mixtures thereof.

29. The composition of any of the preceding embodiments, wherein the nylon comprises nylon 6,6.

30. The composition of any of the preceding embodiments, wherein the nylon is nylon 6,6.

31. The composition of any of the preceding embodiments, wherein at least some of the water is dissolved or dispersed in the liquid.

32. The composition of embodiment 31 wherein concentration of the water dissolved or dispersed in the liquid is between 50 ppm and 300 ppm based on the liquid and any components dissolved or dispersed in the liquid.

33. The composition of any of embodiments 31-32, wherein the nylon pellets having a cylindrical shape.

33a. The composition of any of the preceding embodiments, wherein the total surface area of the one or more nylon components or pellets is between 4 $mm^2$ and 160 $mm^2$ per gram of liquid propellant.

33b. The composition of any of the preceding embodiments, wherein the total surface area of the one or more nylon components or pellets is between 70 $mm^2$ and 1,600 $mm^2$, and the total mass of liquid propellant is between 10 grams and 16 grams.

33c. The composition of any of the preceding embodiments, wherein the total surface area of the one or more nylon components or pellets is between 35 $mm^2$ and 1,000 $mm^2$, and the total mass of liquid propellant is between 4 grams and 10 grams.

34. An aerosol canister containing a formulation of any preceding embodiment under a pressure that is greater than ambient atmospheric pressure.

35. The aerosol canister of embodiment 34 comprising at least one surface having a primer composition comprising a silane having two or more reactive silane groups separated by an organic linker group disposed thereon, wherein the primer composition has a coating composition comprising an at least partially fluorinated compound disposed thereon.

36. The aerosol canister of embodiment 35, wherein the at least partially fluorinated compound is an at least partially fluorinated polyethersilane.

37. An aerosol canister of embodiment 34 comprising at least one surface having a coating comprising polyphenylsulphone.

38. An aerosol canister of embodiment 34 comprising at least one surface having a coating comprising a diamond-like glass or carbon-like glass.

39. An inhaler comprising the formulation of any of embodiments 1-33 or the aerosol canister of any of embodiments 34-38.

40. The inhaler of embodiment 39 that is a metered dose inhaler.

41. The inhaler of any of embodiments 39-40 comprising a valve stem.

42. The inhaler of any of embodiments 39-41 comprising a dose counter.

43. The inhaler of any of embodiments 39-42, comprising at least one nylon component, the at least one nylon component having water absorbed therein or adsorbed thereon.

44. The inhaler of embodiment 43, wherein the at least one nylon component is selected from a valve stem, an O-ring, and a gasket.

45. A moisture barrier pouch comprising at least one moisture barrier layer, the moisture barrier pouch having an interior and an exterior, the interior of the moisture barrier pouch comprising an inhaler of any of embodiments 39-44.

46. The moisture barrier pouch of embodiment 45, wherein the interior of the pouch does not contain a desiccant.

47. The moisture barrier pouch of any of embodiments 45 or 46, wherein the at least one moisture barrier layer comprises aluminum foil.

48. A method of making an inhaler of any of embodiments 39-42 comprising sealing a canister containing a composition of any of embodiments 1-38.

49. The method of embodiment 48, wherein at least a part of the composition of any of embodiments 1-38 is cold-filled into the canister.

50. The method of embodiment 48, wherein at least a part of the composition of any of embodiments 1-38 is filled into the canister under pressure.

51. The method of embodiment 48, wherein at least a part of the composition of any of embodiments 1-38 is filled into the canister under the application of pressure greater than atmospheric pressure.

52. A method of maintaining a water level in a pressurized aerosol canister, the method comprising soaking one or more nylon pellets in water to form one or more water soaked pellets, optionally removing water from the surface of the one or more water soaked pellets, forming an aerosol composition of any of embodiments 1-33 by combining the one or more pellets with a composition comprising a pharmaceutical active agent and a liquid comprising one or more of HFA-134*a* and HFA-227.

adding the aerosol composition to a canister and pressurizing the canister to form an aerosol canister of any of embodiments 34-36.

53. The method of embodiment 52, wherein the water level is a pre-determined water level.

54. A method of maintaining a water level in a pressurized aerosol canister, the method comprising soaking one or more nylon internal components of an inhaler in water to form one or more water soaked nylon components, optionally removing water from the surface of the one or more water soaked nylon components adding the one or more nylon internal components and an aerosol composition of any of embodiments 1-33 to the canister.

55. The method of embodiment 54, wherein the water level is a pre-determined water level.

56. The method of any of embodiments 52-55 wherein the water level or pre-determined water level is between 50 ppm and 500 ppm based on the liquid and any components dissolved or dispersed in the liquid.

EXAMPLES

HFA-134*a* (1,1,1,2-tetrafluoroethane) was obtained from the DuPont Corporation (Wilmington, Del.). HFA-227 (1,1,1,2,3,3,3-heptafluoropropane) was obtained from the Solvay Corporation (Brussels, Belgium). Ipratropium bromide monohydrate was obtained from Sifavitor-Infa Group (Milan, Italy). Albuterol sulfate was obtained from Teva Active Pharmaceutical Ingredients (Petah Tivka, Israel). Deionized water was used.

Rods of nylon 6,6 (5 mm in diameter) were obtained from Direct Plastics Ltd. (Sheffield, UK) and stored under ambient conditions.

Metered dose inhaler canisters were prepared using 15 mL deep drawn aluminum cans and 3M retention valves with EPDM (ethylene-propylene diene terpolymer) elastomer seals both obtained from the 3M Corporation (Clitheroe, UK). For Examples 3 to 5, the internal surface of each can was coated with FEP (fluorinated ethylene propylene copolymer).

In Tables 1-2 and 4-6, the surface area of each nylon pellet was calculated using the equation for calculating the surface area of a right circular cylinder (Equation 1) where r=the radius of the circular end (or base) of the pellet and h=the height (or length) of the pellet. When more than one nylon pellet was added to a canister the "Total Surface Area of Pellet(s)" that is reported is the sum of the surface areas for the added pellets.

$$\text{Surface area of a pellet}=(2\pi rh)+2(\pi r^2) \qquad \text{Equation 1:}$$

The length of each pellet was measured using a digital caliper (Absolute Digimatic, Mitutoyo Corporation, Kawasaki, Japan). When more than one nylon pellet was added to a canister the "Total Length of Pellet(s)" that is reported is the sum of the measured lengths for the added pellets.

Example 1

Pellets of differing lengths were cut from the nylon 6,6 rods using a scalpel and were then soaked in a water bath at room temperature for 12 hours. The pellets were removed from the water bath and their surfaces were thoroughly wiped dry using paper toweling. One or more pellets were then added to an aluminum can and the can was then immediately cold-filled with about 12.5-14 grams of HFA-134*a*. The metering valve was then attached by crimping it to the can to form a finished metered dose inhaler canister. Nine different canisters (canisters 1-9) were prepared according to this procedure, each with a different number of pellets and/or pellet length. Two additional canisters were prepared as comparative examples (A and B) in which the same procedure was followed except that no pellets were added to the canister. The comparative canisters provided a baseline water content for HFA-134*a* filled canisters. The finished canisters were stored in a valve-up orientation at ambient conditions for one month. At the end of the storage period, the water content in the propellant of each canister was determined using a Karl Fischer test. A Karl Fischer coulemetric titrator (Mitsubishi CA-100 model available from the Mitsubishi Chemical Corporation, Tokyo, Japan) was used to determine the water content in the canister. The titration cell contained Anode solution Coulomat AG and Cathode solution Coulomat CG. The instrument was calibrated prior to use with a known amount of a certified 10 mg/ml water standard solution. To determine the amount of water in each canister, an aliquot of the formulation was fired directly from the metering valve into the titration vessel via a metal cannula (needle). The water in the Karl Fischer solution was then titrated and the water concentration was calculated.

In Table 1, for each canister the total length (in mm) of the one or more pellets added to the canister, the total calculated surface area (in mm$^2$) of the one or more pellets added to the canister, and the final water content in the HFA-134-*a* propellant (in ppm) are reported.

TABLE 1

| Finished Canister Designation | Number of pellets added to Canister | Total length of pellet(s) added to Canister (mm) | Total surface area of pellet(s) added to Canister (mm$^2$) | Water Content of HFA-134a after 1 Month of Storage (ppm) |
|---|---|---|---|---|
| Comparative A | 0 | 0 | 0 | 102 |
| Comparative B | 0 | 0 | 0 | 88 |
| 1 | 1 | 2.12 | 72.6 | 185 |
| 2 | 1 | 2.25 | 74.6 | 183 |
| 3 | 1 | 4.13 | 104.1 | 220 |
| 4 | 1 | 6.02 | 133.8 | 260 |
| 5 | 1 | 7.94 | 164.0 | 299 |
| 6 | 2 | 10.29 | 240.2 | 358 |
| 7 | 2 | 18.45 | 368.4 | 442 |
| 8 | 3 | 30.05 | 589.8 | 523 |
| 9 | 8 | 80.57 | 1579.7 | 635 |

Example 2

Finished metered dose inhaler canisters were prepared, stored, and analyzed for water content following the method described in Example 1 with the exception that HFA-227 propellant was added to the cans, instead of HFA-134*a* propellant.

Nine different canisters (canisters 10-18) were prepared according to this procedure, each with a different number of pellets and/or pellet length. Two additional canisters were prepared as comparative examples (C and D) in which the same procedure was followed except that no pellets were added to the canister. The comparative canisters provided a baseline water content for HFA-227 filled canisters. The finished canisters were stored in a valve-up orientation at ambient conditions for one month. At the end of the storage period, the water content in the propellant of each canister was determined using a Karl Fischer test. In Table 2, for each canister the total length (in mm) of the one or more pellets added to the canister, the total calculated surface area (in mm$^2$) of the one or more pellets added to the canister, and the final water content (in ppm) in the HFA-227 propellant are reported.

TABLE 2

| Finished Canister Designation | Number of pellets added to Canister | Total length of pellet(s) added to Canister (mm) | Total surface area of pellet(s) added to Canister (mm$^2$) | Water Content of HFA-227 after 1 Month of Storage (ppm) |
|---|---|---|---|---|
| Comparative C | 0 | 0 | 0 | 75 |
| Comparative D | 0 | 0 | 0 | 75 |
| 10 | 1 | 2.10 | 72.3 | 169 |
| 11 | 1 | 2.25 | 74.6 | 159 |
| 12 | 1 | 4.13 | 104.1 | 179 |
| 13 | 1 | 6.02 | 133.8 | 200 |
| 14 | 1 | 7.94 | 164.0 | 219 |
| 15 | 2 | 10.26 | 239.7 | 254 |
| 16 | 2 | 18.07 | 362.4 | 296 |
| 17 | 3 | 30.21 | 592.3 | 323 |
| 18 | 8 | 80.49 | 1578.5 | 355 |

Example 3

Albuterol sulfate and ipratropium bromide monohydrate were each micronized to provide a mass median diameter (MMD) range of about 1-5 microns. Pellets of differing lengths were cut from the nylon 6,6 rods using a scalpel, and were then soaked in a water bath at room temperature for 24 hours. The pellets were removed from the water bath and their surfaces were thoroughly wiped dry using paper toweling. One or more pellets were then added to an aluminum can and the can was then immediately cold-filled with the drug suspension formulation of Table 3 (albuterol sulfate and ipratropium bromide monohydrate in propellant). The propellant was a pre-mixed solution (50:50 by weight) of HFA-134*a* and HFA-227. The bulk formulation for cold filling individual canisters was prepared by combining the micronized albuterol sulfate and ipratropium bromide monohydrate with a portion of the propellant solution (about half of the total propellant) in a vessel chilled to a temperature below −50° C. The resultant suspension was high shear mixed for 5-10 minutes using a Silverson mixer (Silverson, East Longmeadow, Mass.). The remaining propellant was then added to the chilled vessel, and high shear mixing was continued for an additional 10 minutes.

Each canister was completed by being cold filled with a total of approximately 13-14.5 grams of the formulation, followed by crimping of the metering valve to the can to form a finished metered dose inhaler canister.

Seven different canisters (canisters 19-25) were prepared according to this procedure, with each canister having a single pellet of varying length (pellet lengths ranging from 1.65-18.02 mm). Two additional canisters were prepared as comparative examples (E and F) in which the same procedure was followed except that no pellet was added to the canister. The comparative canisters provided a baseline water content for the canisters filled with the formulation. The finished canisters were stored in a valve-up orientation at ambient conditions for one month. At the end of the storage period, the water content in the formulation of each canister was determined using a Karl Fischer test. In Table 4, for each canister the total length (in mm) of the pellet added to the canister, the total calculated surface area (in mm$^2$) of the pellet added to the canister and the final water content of the formulation (in ppm) are reported.

TABLE 3

Suspension Formulation of Example 3

| Formulation Ingredient | Amount (in Percent by Weight) |
| --- | --- |
| Albuterol sulfate | 0.295 |
| Ipratropium Bromide Monohydrate | 0.052 |
| HFA-134a/HFA-227 (50:50 by weight) | 99.653 |

TABLE 4

| Finished Canister Designation | Number of pellets added to Canister | Total length of pellet(s) added to Canister (mm) | Total surface area of pellet(s) added to Canister (mm$^2$) | Water Content of the Formulation after 1 Month of Storage (ppm) |
| --- | --- | --- | --- | --- |
| Comparative E | 0 | 0.00 | 0.0 | 62 |
| Comparative F | 0 | 0.00 | 0.0 | 62 |
| 19 | 1 | 1.65 | 65.2 | 117 |
| 20 | 1 | 2.62 | 80.4 | 138 |
| 21 | 1 | 4.04 | 102.7 | 141 |
| 22 | 1 | 6.22 | 137.0 | 165 |
| 23 | 1 | 10.19 | 199.3 | 195 |
| 24 | 1 | 14.05 | 260.0 | 230 |
| 25 | 1 | 18.02 | 322.3 | 249 |

Example 4

Finished metered dose inhaler canisters were prepared, stored, and analyzed for water content following the method described in Example 3 with two exceptions. First, the nylon pellets were soaked in water for 12 hours, instead of 24 hours. Second, the total length of the nylon pellets added to a canister was greater than for any of the canisters of Example 3.

Two different canisters (canisters 26-27) were prepared according to this procedure, each with a different number of pellets and/or pellet length. Two additional canisters were prepared as comparative examples (G and H) in which the same procedure was followed except that no pellets were added to the canister. The comparative canisters provided a baseline water content for canisters filled with the formulation. The finished canisters were stored in a valve-up orientation at ambient conditions for one month. At the end of the storage period, the water content in the formulation of each canister was determined using a Karl Fischer test. In Table 5, for each canister the total length (in mm) of the one or more pellets added to the canister, the total calculated surface area (in mm$^2$) of the one or more pellets added to the canister and the final water content of the formulation (in ppm) are reported.

TABLE 5

| Finished Canister Designation | Number of pellets added to Canister | Total length of pellet(s) added to Canister (mm) | Total surface area of pellet(s) added to Canister (mm$^2$) | Water Content of the Formulation after 1 Month of Storage (ppm) |
| --- | --- | --- | --- | --- |
| Comparative G | 0 | 0 | 0 | 113 |
| Comparative H | 0 | 0 | 0 | 117 |
| 26 | 3 | 30.55 | 597.7 | 422 |
| 27 | 8 | 80.40 | 1577.1 | 468 |

Example 5

Finished metered dose inhaler canisters were prepared, stored, and analyzed for water content following the method described in Example 3 with the exception that the nylon pellets were soaked in water for a minimum of 60 hours, instead of 24 hours.

Five different canisters (canisters 28-32) were prepared according to this procedure each with each canister having a single pellet of varying length (pellet lengths ranging from 2.41-10.17 mm). Two additional canisters were prepared as comparative examples (I and J), in which the same procedure was followed except that no pellets were added to the canister. The comparative canisters provided a baseline water content for canisters filled with the formulation. The finished canisters were stored in a valve-up orientation at ambient conditions for one month. At the end of the storage period, the water content in the formulation of each canister was determined using a Karl Fischer test. In Table 6, for each canister the total length (in mm) of the added to the canister, the total calculated surface area (in mm$^2$) of the pellet added to a canister and the final water content of the formulation (in ppm) are reported.

TABLE 6

| Finished Canister Designation | Number of pellets added to Canister | Total length of pellet(s) added to Canister (mm) | Total surface area of pellet(s) added to Canister (mm$^2$) | Water Content of the Formulation after 1 Month of Storage (ppm) |
| --- | --- | --- | --- | --- |
| Comparative I | 0 | 0 | 0 | 113 |
| Comparative J | 0 | 0 | 0 | 117 |
| 28 | 1 | 2.41 | 77.1 | 224 |
| 29 | 1 | 4.28 | 106.5 | 269 |
| 30 | 1 | 6.30 | 138.2 | 318 |
| 31 | 1 | 8.13 | 167.0 | 361 |
| 32 | 1 | 10.17 | 199.0 | 370 |

What is claimed is:

1. A method of making an aerosol composition, the method comprising:
   forming a composition, the composition comprising a liquid comprising a propellant, the propellant comprising one or more of HFA-134a and HFA-227, and one or more pharmaceutical active agents dissolved or dispersed in the liquid, wherein the one or more pharmaceutical active agents is a hydrate,
   soaking one or more nylon pellets in water to form one or more water soaked nylon pellets, wherein at least some of the water is adsorbed on or absorbed within the one or more water soaked nylon pellets,
   removing at least some water from a surface of the one or more water soaked nylon pellets, and
   adding the one or more water soaked nylon pellets obtained from the removing step to the composition to form the aerosol composition.

2. The method of claim 1, wherein at least one of the one or more pharmaceutical active agents is a hydrate of ipratropium or a hydrate of an ipratropium salt.

3. The method of claim 1, wherein at least one of the one or more pharmaceutical active agents is ipratropium bromide monohydrate.

4. The method of claim 1, wherein the composition further comprises albuterol.

5. The method of claim 1, wherein the nylon is nylon 6,6.

6. The method of claim 1, wherein the propellant comprises HFA-134a.

7. The method of claim 1, wherein at least some of the water is dissolved or dispersed in the liquid and the concentration of the water dissolved or dispersed in the liquid is between 50 ppm and 500 ppm based on the liquid and any components dissolved or dispersed in the liquid.

8. The method of claim 1, wherein the step of removing at least some water is accomplished by blotting the water soaked nylon pellets.

* * * * *